(12) United States Patent
Taal et al.

(10) Patent No.: US 12,070,589 B2
(45) Date of Patent: Aug. 27, 2024

(54) AUTOINJECTOR

(71) Applicant: SANOFI-AVENTIS DEUTSCHLAND GMBH, Frankfurt am Main (DE)

(72) Inventors: Stefan Taal, London (GB); Thomas Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 249 days.

(21) Appl. No.: 17/849,222

(22) Filed: Jun. 24, 2022

(65) Prior Publication Data

US 2022/0313926 A1    Oct. 6, 2022

Related U.S. Application Data

(63) Continuation of application No. 17/029,514, filed on Sep. 23, 2020, now Pat. No. 11,369,750, which is a
(Continued)

(30) Foreign Application Priority Data

Jul. 9, 2013    (EP) ..................................... 13175663

(51) Int. Cl.
  *A61M 5/32*    (2006.01)
  *A61M 5/20*    (2006.01)
  *A61M 5/50*    (2006.01)

(52) U.S. Cl.
  CPC ........ *A61M 5/3257* (2013.01); *A61M 5/2033* (2013.01); *A61M 2005/2013* (2013.01);
(Continued)

(58) Field of Classification Search
  CPC .... A61M 2005/2013; A61M 2005/206; A61M 2005/3247; A61M 5/2033; A61M 5/326
  See application file for complete search history.

(56) References Cited

U.S. PATENT DOCUMENTS 10,137,256 B2    11/2018    Taal et al.
2009/0312705 A1    12/2009    Grunhut et al.
(Continued)

FOREIGN PATENT DOCUMENTS

CN    102149419    8/2011
EP    2438942    4/2012
(Continued)

OTHER PUBLICATIONS

Extended European Search Report in Application No. 13175663.7 dated Jan. 2, 2014, 8 pages.
International Preliminary Report on Patentability in International Application No. PCT/EP2014/064426, issued Jan. 12, 2016, 8 pages.
(Continued)

*Primary Examiner* — Deanna K Hall
(74) *Attorney, Agent, or Firm* — Fish & Richardson P.C.

(57) ABSTRACT

An autoinjector includes a case adapted to hold a medicament container, a needle shroud telescopically coupled to the case, and a plunger slidably disposed in the case. The needle shroud is movable between a first extended position, a retracted position, and a second extended position relative to the case. The plunger is movable between a proximal position, an intermediate position, and a distal position relative to the case. When the plunger is in the intermediate position and the needle shroud is in the retracted position, the plunger abuts the case to prevent the needle shroud from returning to the extended position. When the plunger is in the distal position and the needle shroud is in the second extended position, the plunger abuts the case to prevent the needle shroud from returning to the retracted position.

16 Claims, 8 Drawing Sheets

Related U.S. Application Data continuation of application No. 16/157,163, filed on Oct. 11, 2018, now Pat. No. 10,814,074, which is a continuation of application No. 14/903,363, filed as application No. PCT/EP2014/064426 on Jul. 7, 2014, now Pat. No. 10,137,256.

(52) U.S. Cl.
CPC ... *A61M 5/3204* (2013.01); *A61M 2005/3247* (2013.01); *A61M 5/326* (2013.01); *A61M 5/5086* (2013.01); *A61M 2205/581* (2013.01); *A61M 2205/582* (2013.01); *A61M 2205/583* (2013.01)

(56) References Cited

U.S. PATENT DOCUMENTS

| | | |
|---|---|---|
| 2011/0196339 A1 | 8/2011 | Hirschel et al. |
| 2012/0203186 A1 | 8/2012 | Vogt et al. |
| 2014/0207106 A1 | 7/2014 | Bechmann et al. |

FOREIGN PATENT DOCUMENTS

| | | |
|---|---|---|
| JP | 2009-533124 | 9/2009 |
| WO | WO 2007/132353 | 11/2007 |
| WO | WO 2010/017650 | 2/2010 |
| WO | WO 2010/136078 | 12/2010 |
| WO | WO 2013/034984 | 3/2013 |

OTHER PUBLICATIONS

International Search Report and Written Opinion in International Application No. PCT/EP2014/064426, mailed Nov. 10, 2014, 10 pages.

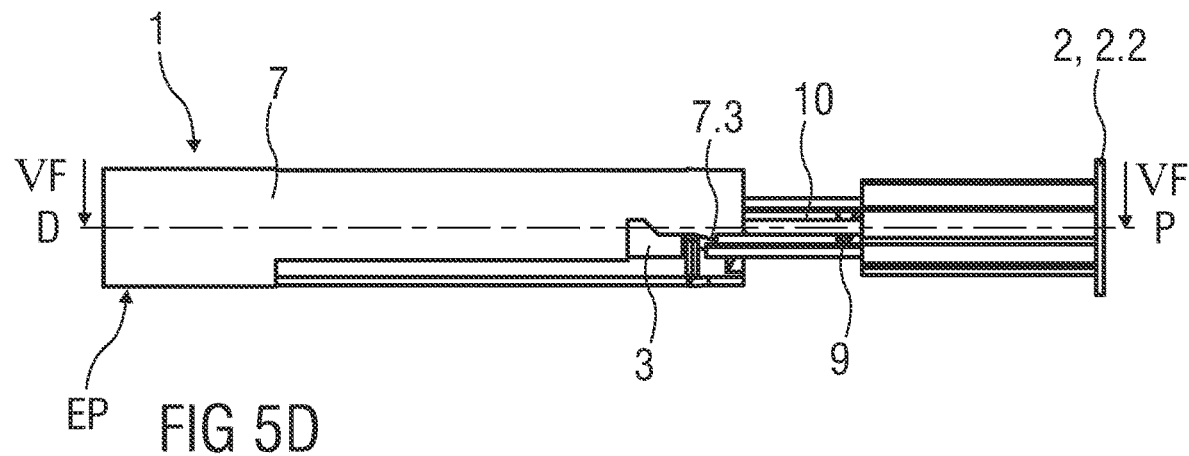
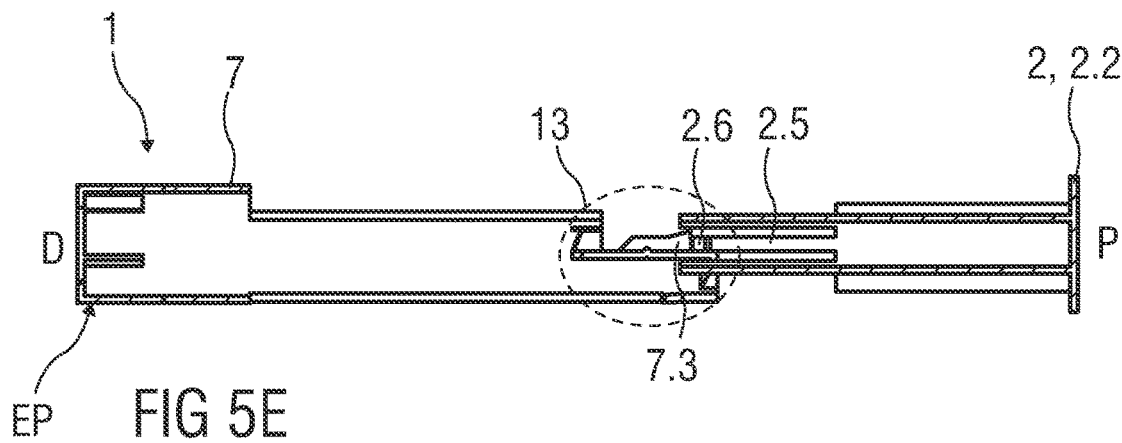
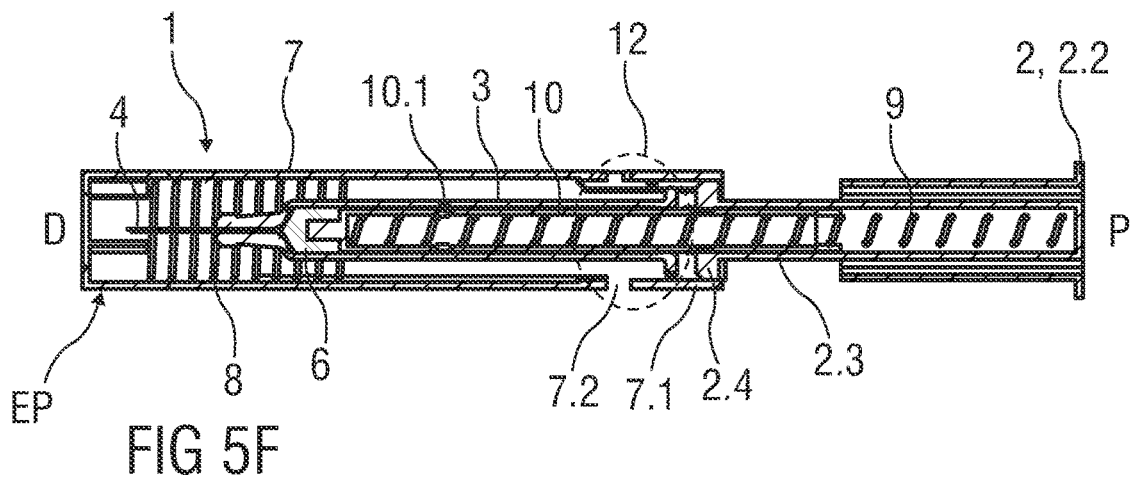

AUTOINJECTOR

CROSS-REFERENCE TO RELATED APPLICATIONS

This application is a continuation of U.S. patent application Ser. No. 17/029,514, filed Sep. 23, 2020, which is a continuation of U.S. patent application Ser. No. 16/157,163, filed Oct. 11, 2018, now U.S. Pat. No. 10,814,074, which is a continuation of U.S. patent application Ser. No. 14/903,363, filed Jan. 7, 2016, now U.S. Pat. No. 10,137,256, which is a U.S. national stage application under 35 USC § 371 of International Application No. PCT/EP2014/064426, filed on Jul. 7, 2014, which claims priority to European Patent Application No. 13175663.7, filed on Jul. 9, 2013, the entire contents of which are incorporated herein by reference.

TECHNICAL FIELD

The invention relates to an autoinjector.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to the present invention comprises a case adapted to hold a medicament container having a needle, a needle shroud telescopically coupled to the case and movable between a first extended position relative to the case in which the needle is covered, and a retracted position relative to the case in which the needle is exposed, and a second extended position relative to the case in which the needle is covered and the needle shroud cannot translate relative to the case, and a plunger slidably disposed in the case and movable between a proximal position, an intermediate position and a distal position relative to the case. When the plunger is in the intermediate position and the needle shroud is in the retracted position, the plunger abuts the case to prevent the needle shroud from returning to the extended position. When the plunger is in the distal position and the needle shroud is in the second extended position, the plunger abuts the case to prevent the needle shroud from returning to the retracted position.

In an exemplary embodiment, the case includes a first compliant case beam having a first boss adapted to engage a radial plunger opening on the plunger when the plunger is in the proximal position. The needle shroud radially abuts the first boss when the needle shroud is in the first extended position. The needle shroud includes a radial shroud opening adapted to accommodate the first boss when the needle shroud is in the retracted position and the first compliant case beam deflects radially.

In an exemplary embodiment, the case includes a second complaint case beam having a second boss adapted to engage a control structure on the needle shroud. The second compliant case beam is movable in radial and tangential directions relative to the case. The control structure includes a first surface adapted to radially abut the second boss when the needle shroud is in the first extended position. The control structure includes a second surface adapted to tangentially abut the second boss when the needle shroud is in the first extended position. The control structure includes a recess proximal of the first surface or the second surface. The recess is adapted to receive the second boss when the needle shroud is in the retracted position and the second compliant case beam deflects radially or tangentially. The plunger abuts the second boss when the second boss is received in the recess and the plunger is in the intermediate position. The control structure includes a third surface radially and tangentially offset from the first surface adapted to radially abut the second boss as the needle shroud translates from the retracted position to the second extended position. The control structure includes a ramped boss proximal of the third surface adapted to tangentially displace the second boss as the needle shroud translates from the retracted position to the second extended position. The control structure includes a notch proximal of the ramped boss adapted to receive the second boss when the needle shroud is in the second extended position and the plunger is in the intermediate position or the distal position. The control structure includes an abutment formed on the first surface or the second surface proximal of the recess adapted to displace the second boss radially or tangentially as the needle shroud translates from the first extended position to the retracted position.

In an exemplary embodiment, the autoinjector further comprises a shroud spring biasing the needle shroud relative to the case.

In an exemplary embodiment, the autoinjector further comprises a drive spring biasing the plunger relative to the case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 5D is a side view of an exemplary embodiment of an autoinjector according to the present invention after use, FIG. 5E is a longitudinal section of an exemplary embodiment of an autoinjector according to the present invention after use, and FIG. 5F is a longitudinal section of an exemplary embodiment of an autoinjector according to the present invention after use.

Corresponding parts are marked with the same reference symbols in all figures.

DETAILED DESCRIPTION

Figure 1A:
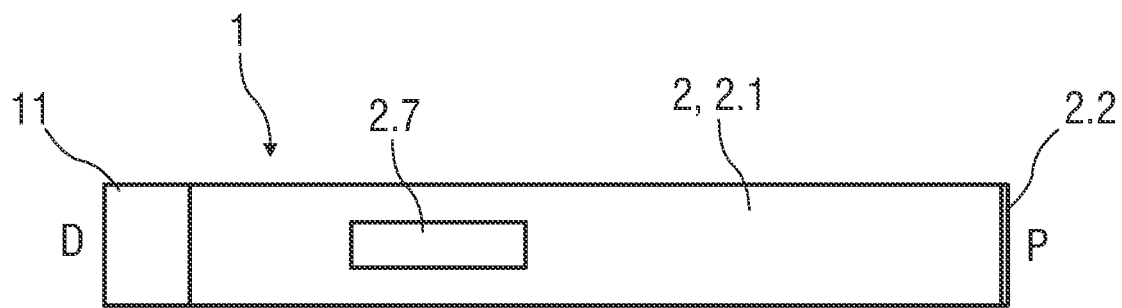
FIG. 1A is a side view of an exemplary embodiment of an autoinjector according to the present invention prior to use.
Figure 1B:
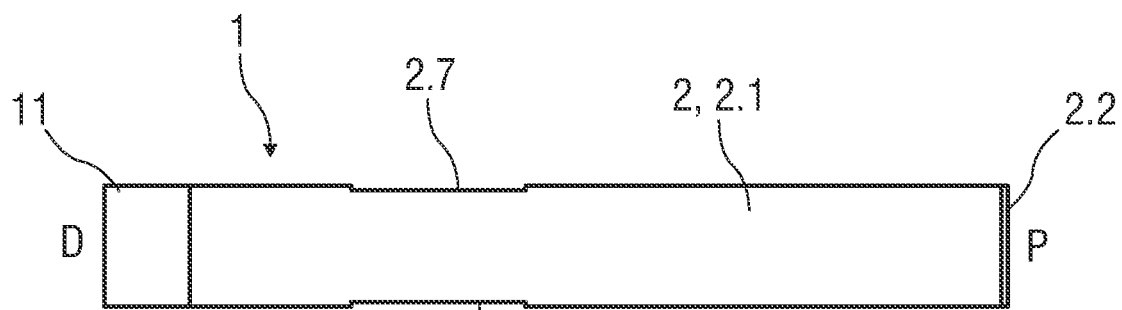
FIG. 1B is a side view of an exemplary embodiment of an autoinjector according to the present invention prior to use.
Figure 1C:
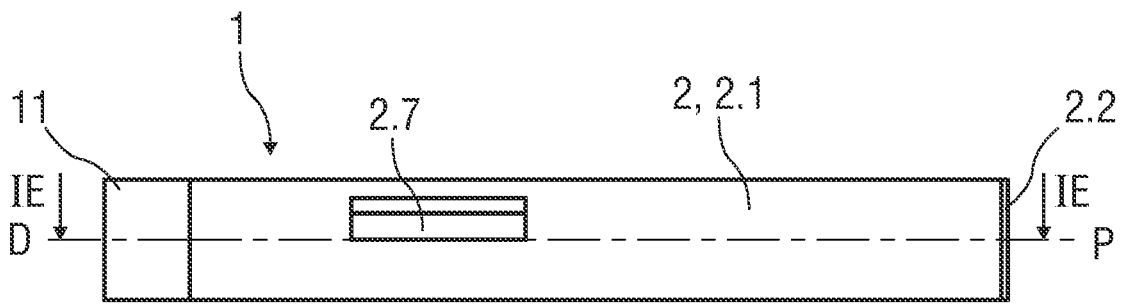
FIG. 1O is a side view of an exemplary embodiment of an autoinjector according to the present invention prior to use.
FIG. 1D is a side view of an exemplary embodiment of an autoinjector according to the present invention prior to use.
FIG. 1E is a longitudinal section of an exemplary embodiment of an autoinjector according to the present invention prior to use.
FIG. 1F is a longitudinal section of an exemplary embodiment of an autoinjector according to the present invention prior to use.
Figure 1D:
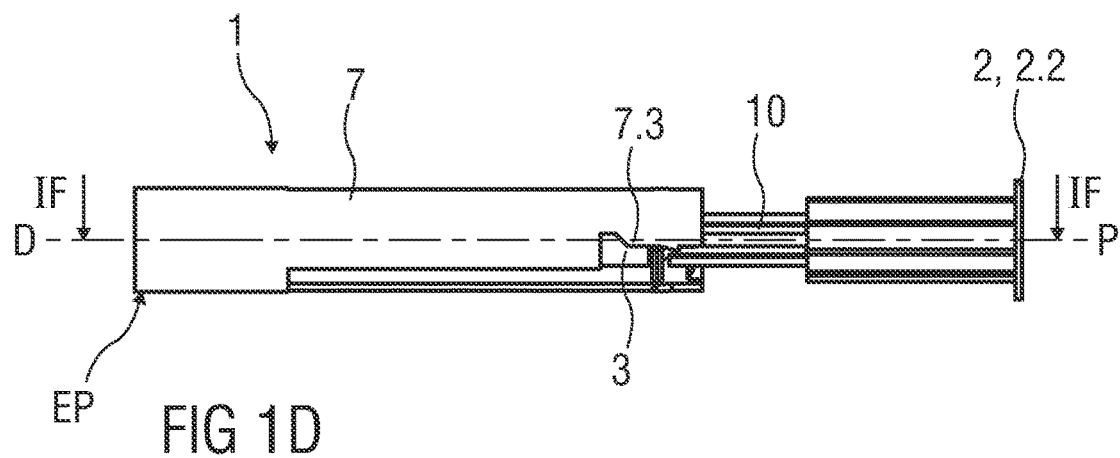
Figure 1E:
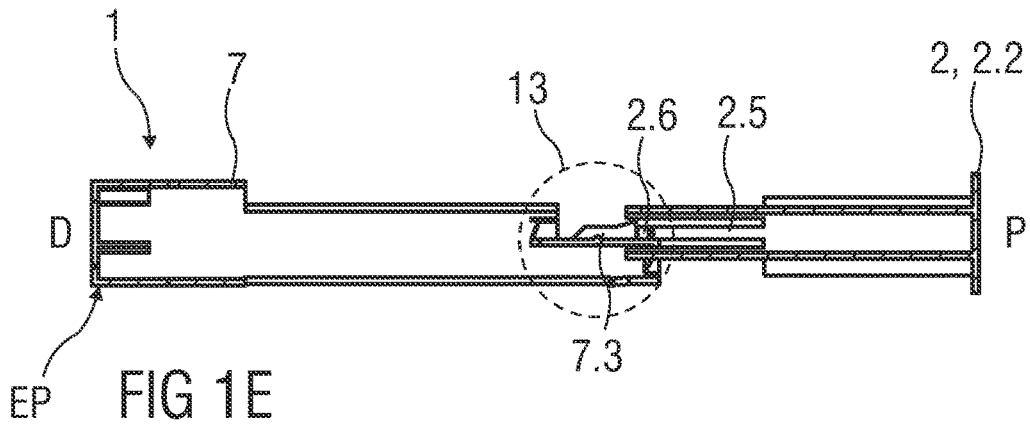
Figure 1F:
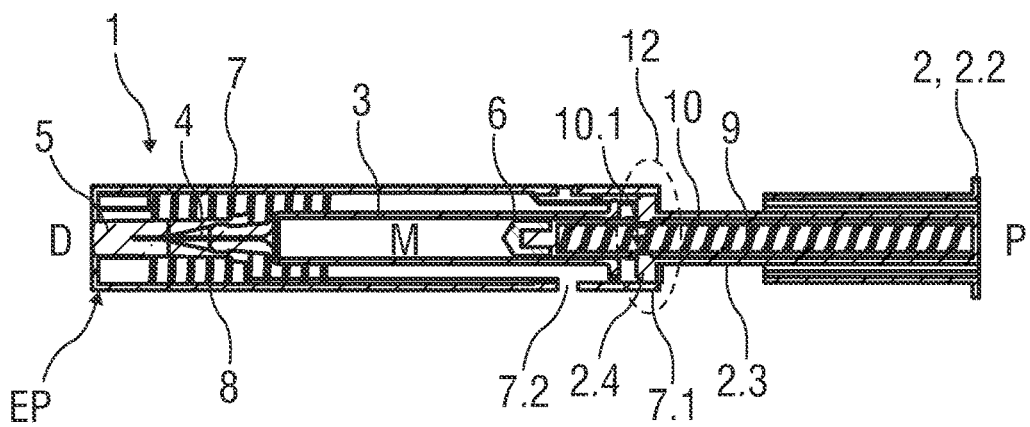

FIGS. 1A, 1B and 1C are different side views of an exemplary embodiment of an autoinjector 1 according to the present invention prior to use. The autoinjector 1 comprises a case 2 including a front case 2.1 and a rear case 2.2. A removable cap 11 is attached at a distal end of the case 2. The case 2 may comprise a viewing window 2.7, which may be a cut-out or transparent portion of the front case 2.1. FIG. 1D is a side view of the autoinjector 1 in the initial state prior to starting an injection with the front case 2.1 of the case 2 removed for clarity. A needle shroud 7 is telescoped within the case 2. FIG. 1E is a longitudinal section of the rear case 2.2 and the needle shroud 7 in the initial state prior to starting an injection. FIG. 1F is a longitudinal section of the autoinjector 1 in the initial state prior to starting an injection with the front case of the case 2 removed for clarity.

As shown in FIG. 1F, the case 2 is adapted to hold a medicament container, such as a syringe 3. The syringe 3 may be a pre-filled syringe and have a needle 4 arranged at a distal end. When the autoinjector 1 and/or the syringe 3 are assembled, a protective needle sheath 5 may be removably coupled to the needle 4. The cap 11 may include an element (e.g., a barb, a hook, a narrowed section, etc.) arranged to engage the protective needle sheath 5 such that the protective needle sheath 5 is removed as the cap 11 is removed from the case 2. A stopper 6 is arranged for sealing the syringe 3 proximally and for displacing a medicament M contained in the syringe 3 through the needle 4. In other exemplary embodiments, the medicament container may be a cartridge which includes the medicament M and engages a removable needle.

In an exemplary embodiment, the needle shroud 7 is biased in a distal direction D relative to the case 2 by a shroud spring 8. Prior to use, the needle shroud 7 is in a first extended position FEP relative to the case 2, extending beyond a distal end of the case 2.

In an exemplary embodiment, a drive spring 9 is disposed within the case 2 and applies a biasing force on a plunger 10 which is adapted to engage the stopper 6. In an exemplary embodiment, the plunger 10 is hollow and the drive spring 9 is arranged within the plunger 10 biasing the plunger 10 in the distal direction D against the case 2.

In an exemplary embodiment, a plunger release mechanism 12 is arranged for preventing release of the plunger 10 prior to depression of the needle shroud 7 and for releasing the plunger 10 once the needle shroud 7 is depressed. In an exemplary embodiment, the plunger release mechanism 12 comprises a compliant first case beam 2.3 with a first boss 2.4 arranged on the case 2, a radial plunger opening 10.1 arranged in the plunger 10 for engaging the first boss 2.4, a proximal end 7.1 of the needle shroud 7 adapted to radially outwardly abut the first boss 2.4 such that it cannot disengage the first opening 10.1 as the needle shroud 7 is in the first extended position FEP, and a radial shroud opening 7.2 in the needle shroud 7 adapted to accommodate the first boss 2.4 when the first case beam 2.3 deflects radially. At least one of the first boss 2.4 and the radial plunger opening 10.1 may be ramped to reduce force necessary to cause the first case beam 2.3 to deflect.

Figure 2:
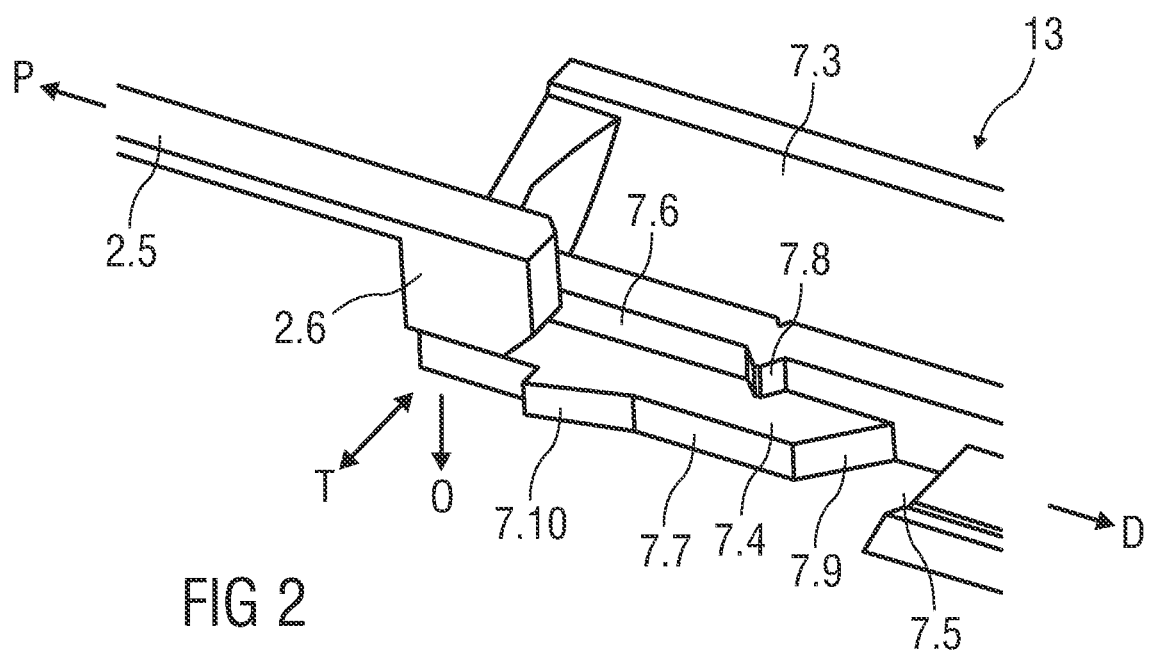
FIG. 2 is a perspective view of an exemplary embodiment of a detent mechanism according to the present invention.
Figure 3A:
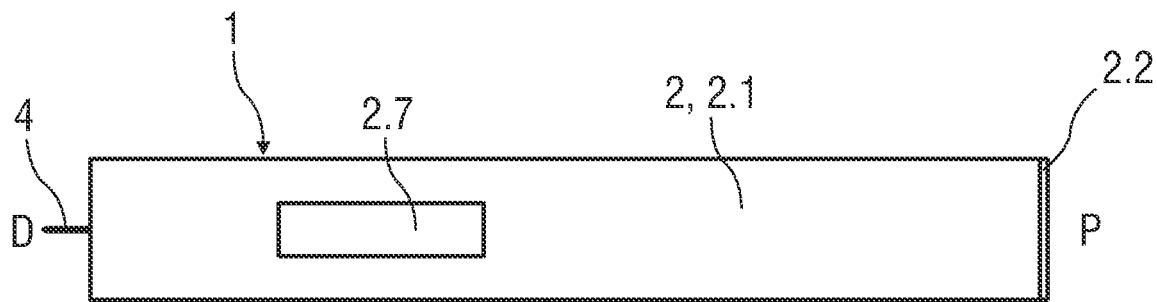
FIG. 3A is a side view of an exemplary embodiment of an autoinjector according to the present invention during use.
Figure 3B:
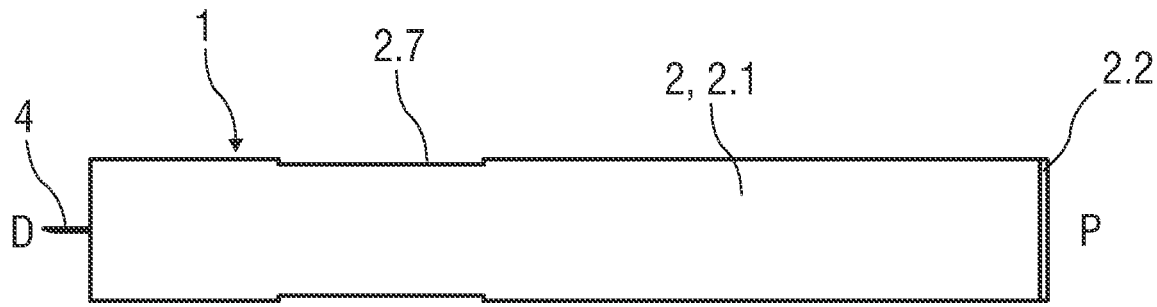
FIG. 3B is a side view of an exemplary embodiment of an autoinjector according to the present invention during use.
Figure 3C:
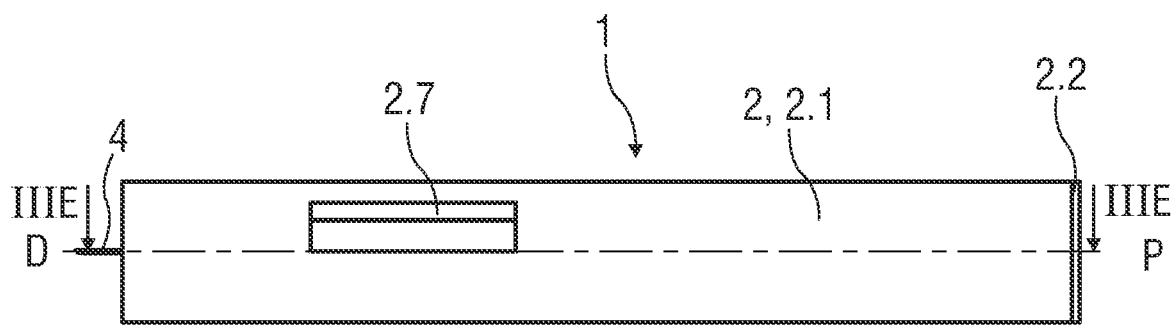
FIG. 3C is a side view of an exemplary embodiment of an autoinjector according to the present invention during use.
Figure 3D:
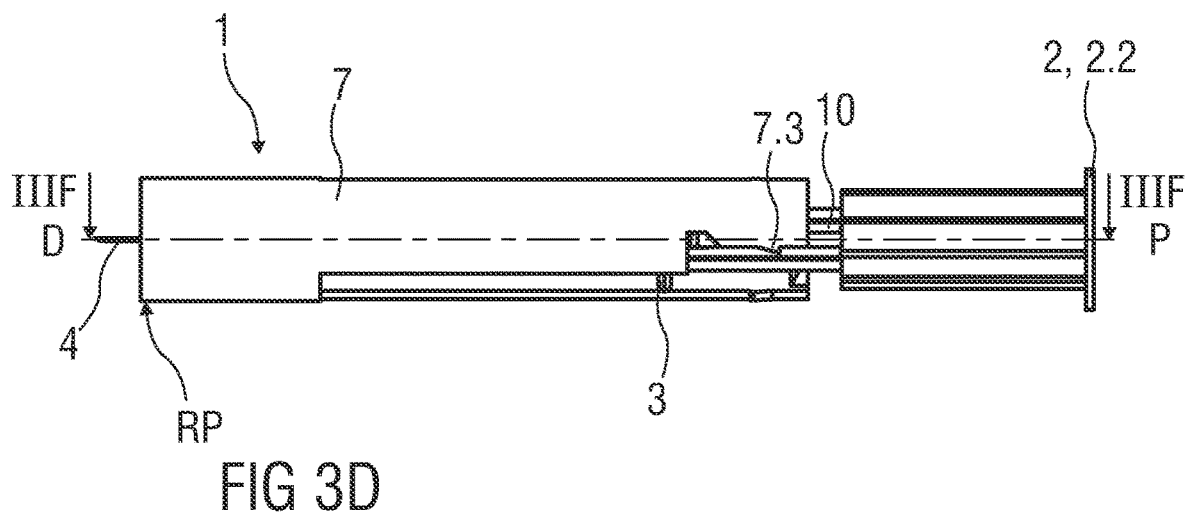
FIG. 3D is a side view of an exemplary embodiment of an autoinjector according to the present invention during use.
Figure 3E:
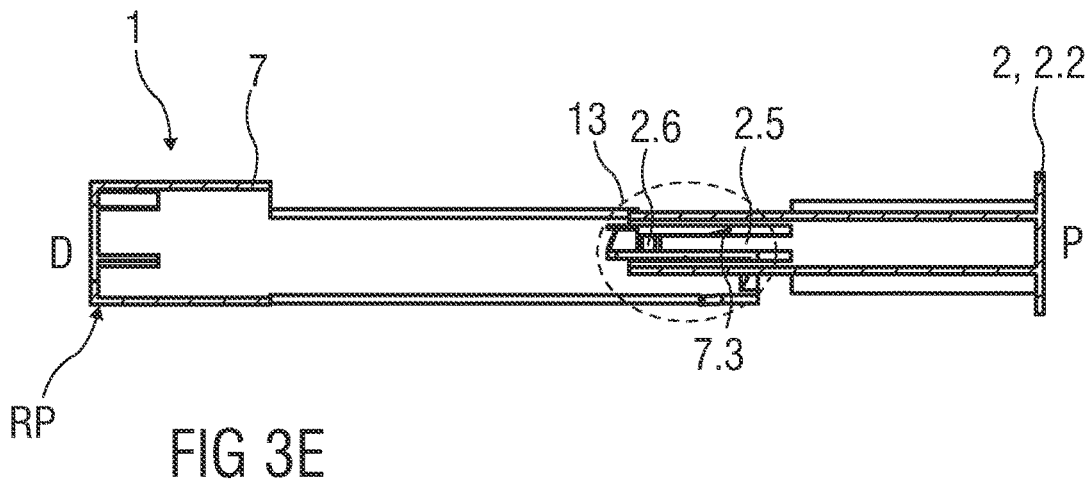
FIG. 3E is a longitudinal section of an exemplary embodiment of an autoinjector according to the present invention during use.
Figure 3F:
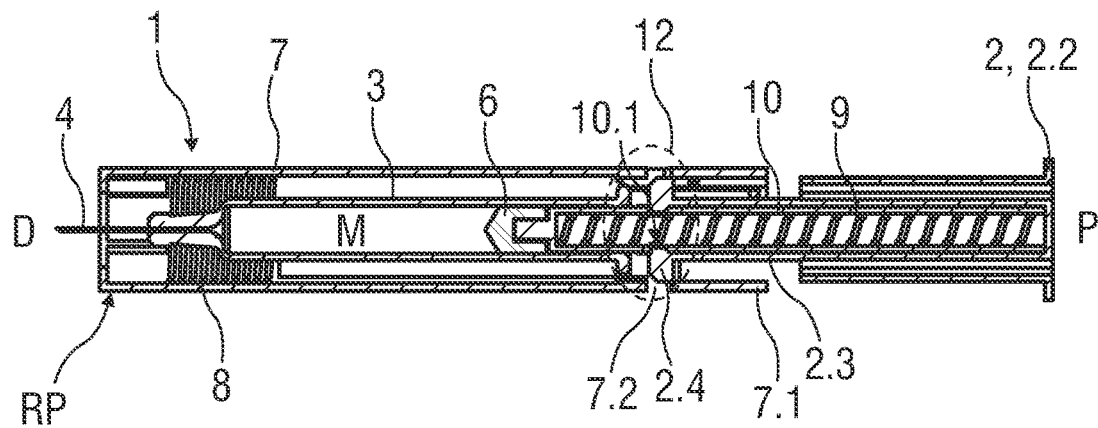
FIG. 3F is a longitudinal section of an exemplary embodiment of an autoinjector according to the present invention during use.

As shown in the exemplary embodiment in FIG. 2, the autoinjector 1 comprises a detent mechanism 13 comprising a compliant second case beam 2.5 with a second boss 2.6 movable in two planes (e.g., a radial direction O and a tangential direction T), and a control structure 7.3 on the needle shroud 7 adapted to interact with the second boss 2.6 depending on a relative axial position of the needle shroud 7 and the case 2. In an exemplary embodiment, the control structure 7.3 comprises a first surface 7.4 adapted to radially abut the second boss 2.6 preventing deflection in a radial outward direction O. A recess 7.5 is arranged to allow deflection of the second boss 2.6 in the radial outward direction O once the recess 7.5 is axially aligned with the second boss 2.6. A tangential second surface 7.6 is arranged adjacent the first surface 7.4, e.g., substantially at right angles, so as to support the second boss 2.6 in one tangential direction T while it is supported by the first surface 7.4 in the radial outward direction O. A tangential third surface 7.7 is arranged adjacent the first surface 7.4 substantially at right angles so as to support the second boss 2.6 in a first tangential direction T after it has been deflected in the radial outward direction O into the third opening 7.5 and is no longer radially supported by the first surface 7.4. The tangential second surface 7.6 may comprise an abutment 7.8 or any other projection, bump or ramp feature arranged to deflect the second boss 2.6 in a second tangential direction T when the second boss 2.6 moves along the second surface 7.6. A ramp 7.9 is arranged to deflect the second boss 2.6 in the second tangential direction T onto the tangential third surface 7.7 once the second boss 2.6 is radially deflected into the third opening 7.5 and subsequently moved in a proximal direction P relative the case 2. The tangential third surface 7.7 may comprise a ramped boss 7.10 arranged to deflect the second boss 2.6 in the second tangential direction T when the second boss 2.6 moves along the tangential third surface 7.7 in the proximal direction P relative to the case 2. When the second boss 2.6 is distal of the ramped boss 7.10, the ramped boss 2.6 may enter a notch and abut the ramped boss 7.10 to prevent the second boss 2.6 from returning in the distal direction D along the third surface 7.7.

In an exemplary embodiment, a sequence of operation of the autoinjector 1 is as follows:

Prior to use the autoinjector 1 is in the state as illustrated in FIGS. 1A to 1F. If applicable, the autoinjector 1 may be removed from a packaging. The medicament M may be examined through the viewing window 2.7, because at least a portion of the syringe 3 may be axially aligned with the viewing window 2.7.

The cap 11 is removed by pulling it in the distal direction D away from the case 2 thereby also removing the protective needle sheath 5. As the syringe 3 is held in the case 2, load exerted by pulling the cap 11 is resolved to the case 2.

FIGS. 3A-F are different views of an exemplary embodiment of the autoinjector 1 during use. When the autoinjector 1 is pressed against an injection site, the needle shroud 7 moves in the proximal direction P relative to the case 2 into a retracted position RP against the bias of the shroud spring 8. As the needle shroud 7 is moving from the first extended position FEP towards the retracted position RP, the second boss 2.6 rides along the radial first surface 7.4 and the tangential second surface 7.6. When the second boss 2.6 engages the abutment 7.8, a first tactile feedback may be provided in the form an increased resistance to continued proximal movement of the needle shroud 7. The first tactile feedback may indicate to a user that further retraction of the needle shroud 7 will commence insertion of the needle 4 into the injection site. If the autoinjector 1 is removed from the injection site prior to needle insertion, the needle shroud 7 will return to the first extended position FEP under the force of the shroud spring 8.

With an increase in applied force, the second case beam 2.5 deflects tangentially, allowing the second boss 2.6 to pass around the abutment 7.8. After passing the abutment 7.8, a second tactile feedback may be provided in the form of a decrease in resistance to continued movement of the needle shroud 7. In a self-administered injection, for example, the decrease in resistance may encourage full needle penetration into the injection site.

When the needle shroud 7 is in the retracted position RP, the first boss 2.4 on the first case beam 2.3 is axially aligned with the radial shroud opening 7.2. Because the first boss 2.4 no longer abuts the needle shroud 7, the force of the drive spring 9 pushes the plunger 10 in the distal direction D, causing the first case beam 2.3 to deflect and thus the first boss 2.4 to deflect radially into the radial shroud opening 7.2 and disengage the radial plunger opening 10.1.

Figure 4A:
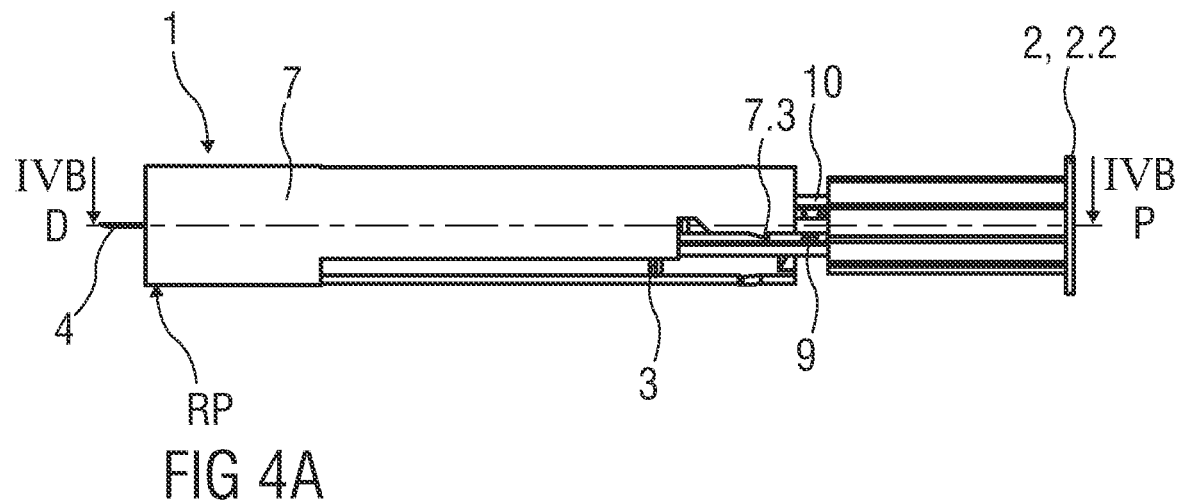
FIG. 4A is a side view of an exemplary embodiment of an autoinjector according to the present invention during use.
Figure 4B:
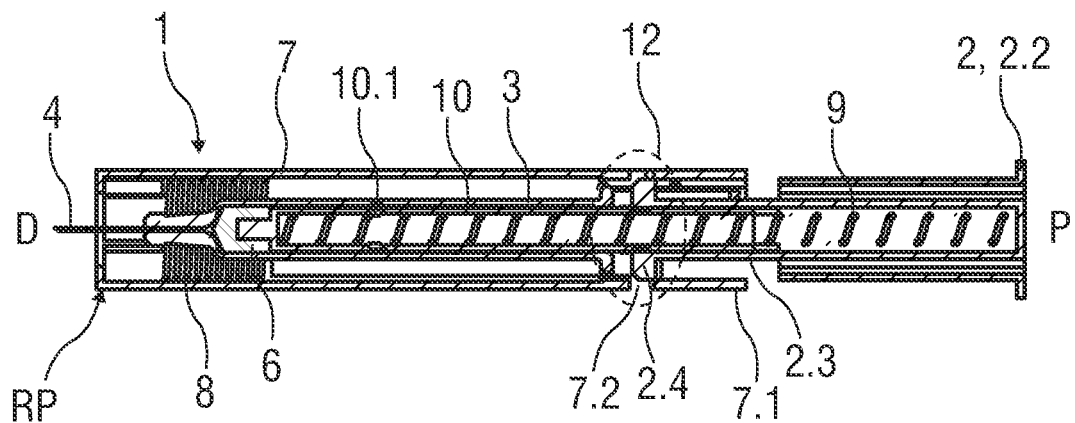
FIG. 4B is a longitudinal section of an exemplary embodiment of an autoinjector according to the present invention during use.
Figure 5A:
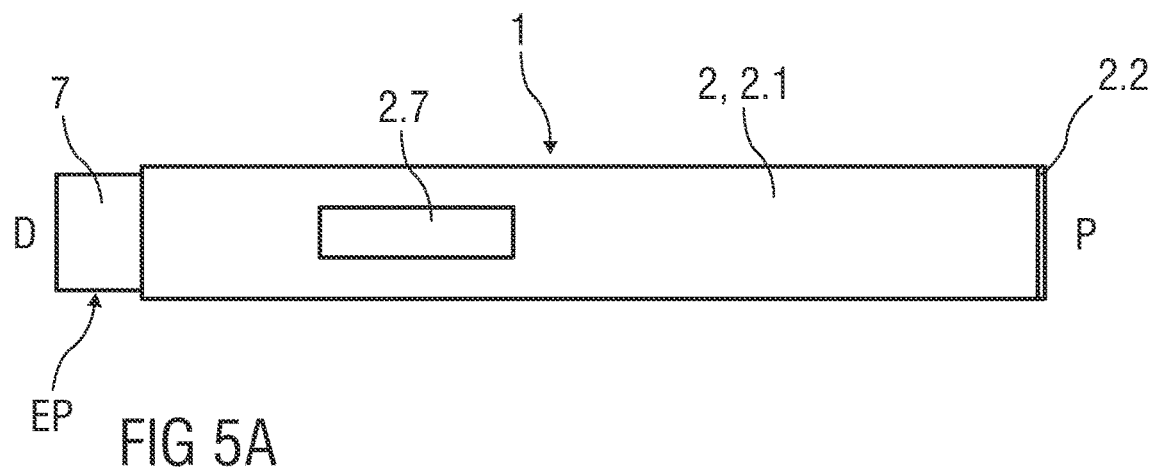
FIG. 5A is a side view of an exemplary embodiment of an autoinjector according to the present invention after use.
Figure 5B:
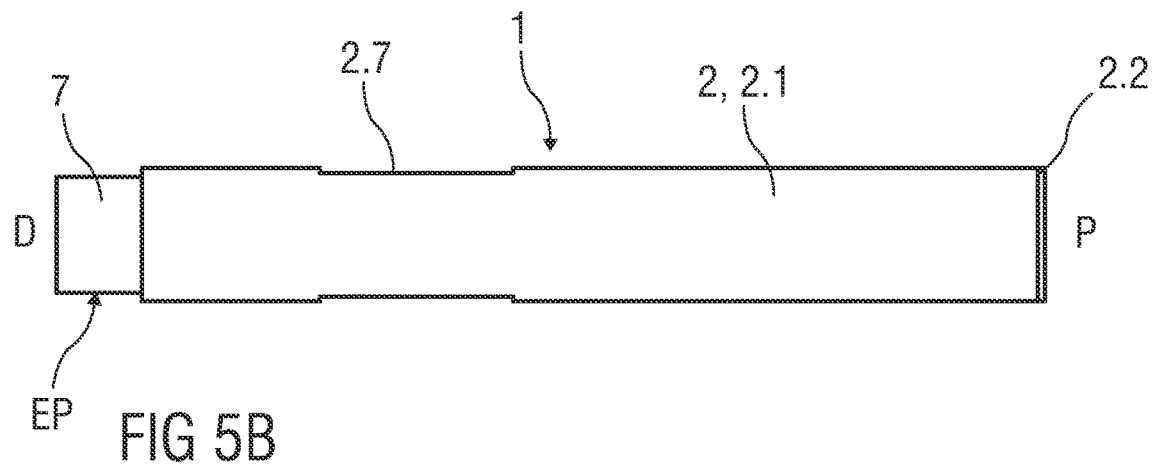
FIG. 5B is a side view of an exemplary embodiment of an autoinjector according to the present invention after use.
Figure 5C:
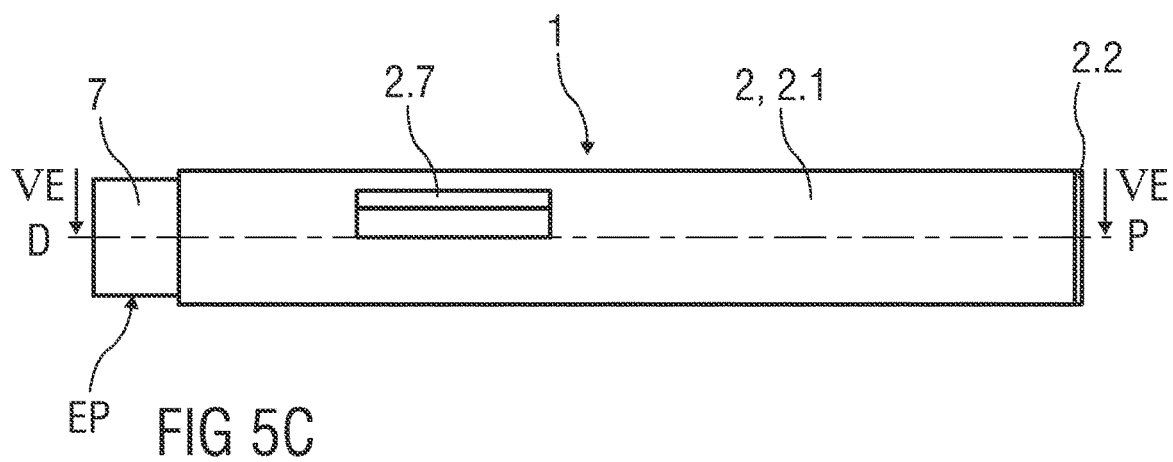
FIG. 5C is a side view of an exemplary embodiment of an autoinjector according to the present invention after use.

As shown in the exemplary embodiments in FIGS. 4A and 4B, when the first boss 2.4 disengages the radial plunger opening 10.1, the plunger 10 is released from a proximal position, translates through an intermediate position and advances the stopper 6 in the distal direction D displacing the medicament M from the syringe 3 through the needle 4. FIGS. 4A and 4B show the plunger 10 in a distal position after the stopper 6 has been advanced through the syringe 3.

When the needle shroud 7 is in the retracted position RP, the recess 7.5 is axially aligned with the second boss 2.6. In an exemplary embodiment, the second case beam 2.5 may be in a deflected state prior to use in that the second boss 2.6 is applying a radial force on the first surface 7.4. Thus, when the recess 7.5 is axially aligned with the third opening 7.5, the second case beam 2.5 may return to its non-deflected state, and the second boss 2.6 may engage the recess 7.5. When the plunger 10 is released, the second boss 2.6 may abut the plunger 10 to prevent the second boss 2.6 from being displaced radially. In another exemplary embodiment, when released, a portion of the plunger 10 may abut the second boss 2.6 and cause the second case beam 2.5 to deflect, causing the second boss 2.6 to engage and be maintained in the recess 7.5. In any embodiment, deflection of the first boss 2.4 and/or the second boss 2.6 may provide an audible feedback to indicate that delivery of the medicament M has started. Axial translation of the plunger 10 can be observed through the viewing window 2.7 for visual confirmation of medicament delivery.

FIGS. 5A-F show an exemplary embodiment of the autoinjector 1 after use. When the autoinjector 1 is removed from the injection site, the needle shroud 7 moves from the retracted position RP towards a second extended position SEP driven by the shroud spring 8 thus covering the needle 4. As the needle shroud 7 moves from the retracted position RP towards the second extended position SEP, the second boss 2.6 rides along the ramp 7.9, causing the second beam 2.5 to deflect in the second tangential direction onto the tangential third surface 7.7. The second boss 2.6 rides along the tangential third surface 7.7 until it engages the ramped boss 7.10, causing the second beam 2.5 to deflect further in the second tangential direction. After the second boss 2.6 bypasses the ramped boss 7.10, the second boss 2.6 engages a notch proximal of the ramped boss 7.10, allowing the second beam 2.5 to deflect in the first tangential direction. The needle shroud 7 thus returns to, and is locked in the second extended position SEP. If the needle shroud 7 attempts to move proximally relative to the case 2 from the second extended position SEP after use, the ramped boss 7.10 abuts the second boss 2.6.

If the autoinjector 1 is removed from the injection site prior to full medicament delivery, the needle shroud 7 will likewise return to the second extended position SEP and lock out, provided the needle shroud 7 has been depressed sufficiently far to release the plunger 10 and the second boss 2.6 has engaged the recess 7.5. Hence, the risk of post-injection needle stick injury is reduced.

The plunger 10 is visible through the viewing window 2.7 thus providing visual confirmation that the autoinjector 1 has been used.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6—NH2,
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector, comprising:
a case adapted to hold a medicament container having a needle;
a plunger having at least one radial plunger opening;
a drive spring arranged to drive the plunger, when the plunger is released, in a distal direction relative to the case;
a needle shroud telescopically coupled to the case and movable between an initial position relative to the case in which the needle is covered by the needle shroud and a retracted position relative to the case in which the needle is exposed; and a plunger release mechanism arranged to prevent release of the plunger when the needle shroud is in the initial position, wherein the plunger release mechanism comprises at least one case boss, wherein the at least one case boss is radially movable and engages the at least one radial plunger opening to prevent release of the plunger when the needle shroud is in the initial position, wherein, for releasing the plunger, the needle shroud is movable towards the retracted position to enable that the at least one case boss disengages the at least one radial plunger opening by removing a radial support from the at least one case boss, and wherein the radial support is removed from the at least one case boss by axially displacing the radial support away from the at least one case boss when the needle shroud is moved towards the retracted position.

2. The autoinjector of claim 1, wherein the plunger is hollow and at least a portion of the drive spring is received within the plunger.

3. The autoinjector of claim 1, wherein the radial plunger opening is arranged closer to a distal end of the plunger than to a proximal end of the plunger.

4. The autoinjector of claim 1, wherein, when the needle shroud is in the retracted position, a distal end of the at least one case boss is arranged distally with respect to a proximal end of the needle shroud.

5. The autoinjector of claim 4, wherein, when the needle shroud is in the retracted position, the at least one case boss is enabled to move radially outwardly with respect to the plunger and radially towards the needle shroud to release the plunger.

6. The autoinjector of claim 1, wherein the autoinjector comprises a cap operatively coupled to a needle sheath covering the needle, the cap being removable from the autoinjector together with the needle sheath, wherein the case is arranged to resolve the force transferred to the medicament container when the cap is removed from the autoinjector together with the needle sheath.

7. The autoinjector of claim 1, wherein the needle shroud, when the needle shroud is in the retracted position, is biased towards the initial position by a shroud spring.

8. The autoinjector of claim 7, wherein the plunger is released for a dispensing operation when the needle shroud is in the retracted position, and wherein, after the dispensing operation, the needle shroud is arranged to be moved by the shroud spring towards the initial position.

9. The autoinjector of claim 8, wherein, after the dispensing operation, the needle shroud is arranged to be moved by the shroud spring relative to the case into a final position.

10. The autoinjector of claim 9, wherein, in the final position, the needle shroud covers the needle.

11. The autoinjector of claim 9, wherein, in the final position, the needle shroud is locked.

12. The autoinjector of claim 1, wherein the case comprises a viewing window.

13. The autoinjector of claim 12, wherein, during a dispensing operation of the autoinjector in which the plunger is released, the plunger becomes visible through the viewing window, the plunger remaining visible through the viewing window after completion of the dispensing operation to provide visual confirmation that the autoinjector has been used.

14. The autoinjector of claim 1, wherein the medicament container is arranged in the case and the medicament container is a syringe.

15. The autoinjector of claim 14, wherein the medicament container contains a medicament.

16. The autoinjector of claim 1, wherein, when the needle shroud is in the retracted position, the at least one case boss is arranged distally relative to the radial support.

* * * * *